United States Patent
Carey et al.

(10) Patent No.: US 10,409,791 B2
(45) Date of Patent: Sep. 10, 2019

(54) DATA COMMUNICATION AND STORAGE SYSTEMS AND METHODS

(71) Applicant: Intertrust Technologies Corporation, Sunnyvale, CA (US)

(72) Inventors: W. Knox Carey, Mountain View, CA (US); Jarl A. Nilsson, Mountain View, CA (US); Eric Swenson, Soquel, CA (US); Bart Grantham, Mountain View, CA (US)

(73) Assignee: Intertrust Technologies Corporation, Sunnyvale, CA (US)

(*) Notice: Subject to any disclaimer, the term of this patent is extended or adjusted under 35 U.S.C. 154(b) by 224 days.

(21) Appl. No.: 15/669,401

(22) Filed: Aug. 4, 2017

(65) Prior Publication Data

US 2018/0039658 A1 Feb. 8, 2018

Related U.S. Application Data

(60) Provisional application No. 62/371,516, filed on Aug. 5, 2016.

(51) Int. Cl.
| | | |
|---|---|---|
| *G06F 16/21* | (2019.01) | |
| *G06F 16/18* | (2019.01) | |
| *G06F 16/22* | (2019.01) | |
| *G16B 50/00* | (2019.01) | |
| *G16B 50/50* | (2019.01) | |
| *G16B 30/10* | (2019.01) | |

(52) U.S. Cl.
CPC ........ *G06F 16/219* (2019.01); *G06F 16/1873* (2019.01); *G06F 16/2282* (2019.01); *G16B 50/00* (2019.02); *G16B 30/10* (2019.02); *G16B 50/50* (2019.02)

(58) Field of Classification Search
CPC .... G06F 16/219; G06F 16/1873; G16B 50/50
See application file for complete search history.

(56) References Cited

U.S. PATENT DOCUMENTS

| | | | | |
|---|---|---|---|---|
| 2005/0214811 A1* | 9/2005 | Margulies | .............. | G16B 20/00 435/6.16 |
| 2013/0091126 A1* | 4/2013 | Krishnaswami | .... | G06F 16/9038 707/722 |
| 2014/0278133 A1* | 9/2014 | Chen | ...................... | G16B 20/00 702/19 |
| 2015/0073719 A1* | 3/2015 | Glynias | .............. | G01N 33/5308 702/19 |
| 2016/0048542 A1* | 2/2016 | Gluzman Peregrine | ..................... | G06F 16/215 707/692 |
| 2016/0092631 A1* | 3/2016 | Yandell | .................. | G16B 20/00 702/19 |
| 2016/0371431 A1* | 12/2016 | Haque | ................... | G16B 20/00 |
| 2017/0076047 A1* | 3/2017 | Adams | ................... | G16H 50/20 |

* cited by examiner

*Primary Examiner* — Kris E Mackes
(74) *Attorney, Agent, or Firm* — Finnegan Henderson Farabow Garrett & Dunner, LLP

(57) ABSTRACT

This disclosure relates to systems and methods for communicating and storing data that may include genomic data. In certain embodiments, a sample genome may be stored and/or communicated as a list of variants relative to a reference dataset. Transmission and/or storage of a set of variants relative to a reference genome may allow for more efficient storage and/or communication of the sample genome. Systems and methods are further disclosed that allow for the efficient selection and computation of a reference dataset used to represent a set of sample genomes.

17 Claims, 5 Drawing Sheets

DATA COMMUNICATION AND STORAGE SYSTEMS AND METHODS

RELATED APPLICATIONS

This application claims the benefit of priority under 35 U.S.C. § 119(e) to U.S. Provisional Patent Application No. 62/371,516, filed Aug. 5, 2016, and entitled "DATA COMMUNICATION AND STORAGE SYSTEMS AND METHODS," the content of which is herein incorporated by reference in its entirety.

COPYRIGHT AUTHORIZATION

Portions of the disclosure of this patent document may contain material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

SUMMARY

The present disclosure relates generally to the communication and storage of data. More specifically, but not exclusively, the present disclosure relates to systems and methods for efficient communication and storage of genomic data.

Genetic testing is moving from detection of Single Nucleotide Polymorphisms ("SNPs")—isolated individual chemical differences in genetic code—to Whole Genomic Sequencing ("WGS"), which records every base pair in a genetic sequencing. Genomic sequencing information may be utilized in connection with a variety of applications including, for example, molecular and evolutionary biology studies. For example, in molecular biology studies, genomic information may be utilized in connection with identifying new genes, identifying potential drug targets, identifying genetic associations with certain diseases and/or conditions, and/or the like.

Genomic data, including the genomes of human beings, tumors, and/or viruses can be very large (e.g., 3 billion base pairs). Three billion base pairs may be electronically encoded in approximately 700 megabytes of data. Given this relatively large size, communicating and/or storing a large number of genomic datasets may require significant communication and/or storage capacity.

Genomes of a given species may be largely similar with the exception of a number of variants. Embodiments of the systems and methods disclosed herein may realize data storage and/or communication efficiencies by storing and/or communicating differences between a reference dataset and a particular sample genome. Such differences may be referred to as variants. In some embodiments, a particular genome sample may be stored and/or communicated as a list of variants relative to a particular reference dataset. Transmission and/or storage of a set of variants relative to a reference dataset may be less costly in terms of amount of data and/or required communication channel bandwidth than transmission and/or storage of the entire sample genome. If required, a system may reconstruct a particular genome sample by applying the set of stored and/or received variants to the reference dataset.

BRIEF DESCRIPTION OF THE DRAWINGS

The inventive body of work will be readily understood by referring to the following detailed description in conjunction with the accompanying drawings, in which.

DETAILED DESCRIPTION

Figure 1:
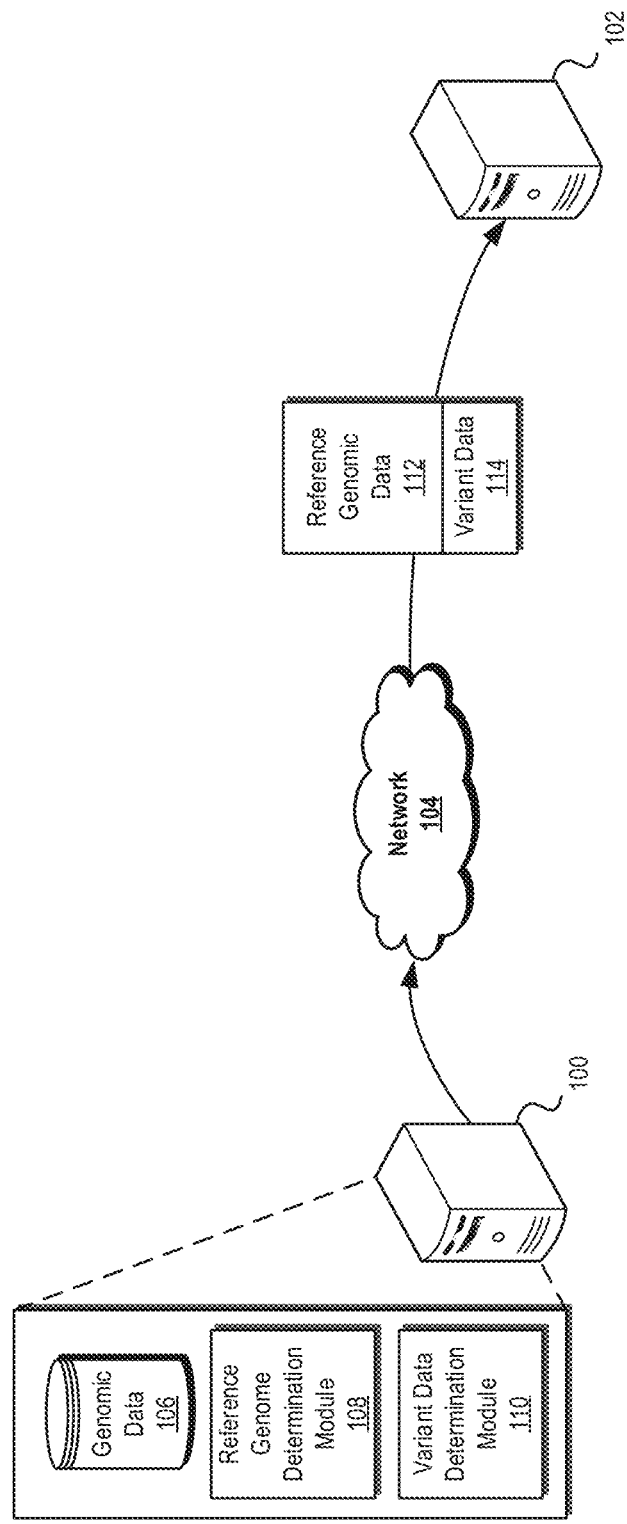
FIG. 1 illustrates an architecture facilitating communication and storage of genomic data consistent with embodiments of the present disclosure.

A detailed description of the systems and methods consistent with embodiments of the present disclosure is provided below. While several embodiments are described, it should be understood that the disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

The embodiments of the disclosure may be understood by reference to the drawings, wherein like parts may be designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of any method disclosed herein do not necessarily need to be executed in any specific order, or even sequentially, nor need the steps be executed only once, unless otherwise specified.

Systems and methods are presented that may facilitate efficient communication and storage of genomic and/or bioinformatic information. In certain embodiments, a particular sample genome may be stored and/or communicated as a list of variants relative to a particular reference genome dataset. Transmission and/or storage of a set of variants relative to a reference dataset may allow for more efficient storage and/or communication of the sample genome. In further embodiments, systems and methods are disclosed that may allow for efficient selection and/or computation of one or more reference datasets for a set of sample genomes.

To communicate a set of sample genomes between systems (e.g., via a network), the set of variant lists associated with the set of genomes and an identifier of an associated reference genome or dataset for each variant list may be transmitted between the systems. In some embodiments, associated reference datasets may be communicated to a receiving system if it does not already possess the reference datasets. In further embodiments, a set of variants may be communicated relative to a base reference genome or dataset so that a given reference dataset may be generated based on the base reference dataset. In certain embodiments, reference datasets, reference dataset variant lists, and/or base reference datasets may be sent to a receiving system in advance of communicating a set to genomes of the system and/or following communication of the set of reference genomes to the system (e.g., based on a request and/or the like).

FIG. 1 illustrates an architecture facilitating communication and storage of genomic data 106 consistent with embodiments of the present disclosure. As used herein, the terms "datasets," "genomic data," "genomic information," "genome," and/or "genomic datasets" may generally refer to data expressing, representing, and/or derived from the entirety or a portion of a genome or genome sequence and, in certain instances herein, may be used interchangeably. This data may include, without limitation, information encoded in chemical structures such as DNA, mRNA, and proteins as well as related regulatory information such as methylation status. As used herein, the term "genome" may refer to an organism's hereditary information. A genome may be encoded in DNA or RNA, and may be represented as mRNA or as protein sequences derived from these nucleic acid sequences. The term "genome" may include both genes and non-coding sequences. When applied to a specific organism, the term "genome" can refer to genomic data from normal cells—including mitochondrial DNA—and also genomic data from related cells such as tumors and other organisms of the microbiome. Although embodiments of the disclosed systems and methods are discussed herein in connection with genomic data 106, it will be appreciated that the disclosed systems and methods may also be used in connection with any other suitable information and/or data including any other type of bioinformatic information. For example, various disclosed embodiments may be employed in connection with any suitable data, and may particularly useful in connection with data having relatively lower variability between various datasets.

One or more genomic data storage and/or processing systems 100, 102 may provide a variety of functions allowing a user to process, analyze, and/or otherwise interact with genomic data 106. The one or more genomic data storage and/or processing systems 100, 102 may, among other things, be configured to store and/or manage genomic data 106 and/or interact with one or more other systems in connection with the same. In certain embodiments, a client system may be associated with a service and/or an application or process that may access and/or otherwise remotely use information stored by the one or more genomic data storage and/or processing systems 100, 102 to perform various operations thereon. For example, an application executing on a client system (not shown) may enable a user of the system to interact with the one or more genomic data storage and/or processing systems 100, 102 in connection with performing various workflow processes and/or analyses using genomic data 106 stored thereon.

The genomic data storage and/or processing systems 100, 102 may be communicatively coupled via a network 104. The network 104 may comprise a variety of network communication devices and/or channels and may utilize any suitable communication protocols and/or standards facilitating communication between the various systems. The network 104 may comprise the Internet, a local area network, a virtual private network, and/or any other communication network utilizing one or more electronic communication technologies and/or standards (e.g., Ethernet or the like). In some embodiments, the network 104 may comprise a wireless carrier system, such as a personal communications system ("PCS"), and/or any other suitable communication system incorporating any suitable communication standards and/or protocols. In further embodiments, the network may comprise an analog mobile communications network and/or a digital mobile communications network utilizing, for example, code division multiple access ("CDMA"), Global System for Mobile Communications or Groupe Speciale Mobile ("GSM"), frequency division multiple access ("FDMA"), and/or time divisional multiple access ("TDMA") standards. In certain embodiments, the network 104 may incorporate one or more satellite communication links. In yet further embodiments, the network may utilize IEEE's 802.11 standards, Bluetooth®, ultra-wide band ("UWB"), Zigbee®, and/or any other suitable standard or standards.

The various systems 100, 102 may comprise a variety of computing devices and/or systems, including any computing system or systems suitable to implement the systems and methods disclosed herein. For example, the systems 100, 102 may comprise a variety of computing devices and systems, including laptop computer systems, desktop computer systems, server computer systems, distributed computer systems, smartphones, tablets, and/or the like. It will be appreciated that any suitable configuration of computing systems and storage media could be used in connection with the systems 100, 102 including without limitation, a single server or cluster of servers, or a distributed collection of heterogeneous computer systems connected by a variety of networks (e.g., such as the Internet, public and/or private networks, and/or the like).

In certain embodiments, the various systems 100, 102 may comprise at least one processor system configured to execute instructions stored on an associated non-transitory computer-readable storage medium. As discussed in more detail below, the various systems 100, 102 may further comprise a secure processing unit ("SPU") configured to perform sensitive operations such as trusted credential and/or key management, secure policy management, and/or other aspects of the systems and methods disclosed herein. The systems 100, 102 may further comprise software and/or hardware configured to enable electronic communication of information between the devices and/or systems via the network 104 using any suitable communication technology and/or standard.

In certain embodiments, a user of a first system 100 may wish to communicate a set of genomic data 106 to a second system 102. Similarly, the second system 102 may request that the first system 100 transmit the genomic data 106 so that the second system 102 may use and/or otherwise store the set of genomic data 106. Consistent with embodiments disclosed herein, to more efficiently communicate and/or store the genomic data 106, the genomic data 106 and/or portions thereof (e.g., individual sample genomic datasets) may be compared with reference genomic data 112 to generate variant data 114, associated with the genomic data 106, which may comprise a list of differences (i.e., variants) between the genomic data 106 and the reference genomic data 112. In certain embodiments, the variant data 114 may be generated by a variant data determination module 110 executing on the first system configured to compare sample genomic data included in the genomic data 106 with a reference dataset (e.g., reference genomic data 112) to generate a list of variants between the two datasets. The list of variants may be communicated from the first system 100 to the second system 102 as part of variant data 114.

In some embodiments, the second system 102 may store and/or otherwise access the reference genomic data used to generate the received variant data 114. For example, as discussed below, the second system may store and/or otherwise access a standard reference genomic dataset used to generate variant data 114. If the second system does not already store and/or otherwise have access to the reference genomic dataset 112, the first system 100 may further communicate the reference genomic data 112 used to generate the variant data 114 to the second system 102. Based on variant data 114 and the reference genomic data 112, the second system 102 may reconstruct the sample genomic data by applying the variant data 114 to the reference genomic dataset 112.

Any suitable reference genome and/or genomic dataset may be used in connection with embodiments of the disclosed systems and methods. In certain embodiments, a single reference genome may be used as a baseline for representing variants in a collection of genomic samples whose genetic information is to be stored, retrieved, transmitted, and/or otherwise used. For example, in some embodiments, a standard reference genome, such as the Genome Reference Consortium human genome, build 38 ("CRCh38") may be used as a reference genome. Certain accepted standard reference genomes, however, may not represent an average genome from which differences with all human beings, or even a certain sample of genomes, is bounded by some size (e.g., a minimum size or the like). To improve efficiency in connection with storing and/or communicating a large set of sample genomes, a reference dataset may be generated and/or selected that reduces the number of variants between sample genomes in the genomic data 106 to be transferred and the reference dataset.

Consistent with embodiments disclosed herein, one or more improved reference datasets may be generated for a set of sample datasets included in genomic data 106 to be transferred and/or stored. In certain embodiments, the generated reference dataset(s) may reduce a number of variants between sample genomic data included in the genomic data 106 and the generated reference dataset(s). In this manner, the size of associated variant data 114 used to represent the genomic data 106 may be reduced, thereby allowing for more efficient transmission and/or storage of the information used to represent the genomic data 106 (e.g., generated reference dataset(s) and associated variant data 114).

It will be appreciated that a number of variations can be made to the architecture and relationships presented in connection with FIG. 1 within the scope of the inventive body of work. For example, without limitation, in some embodiments, some or all of the functions performed by the genomic data storage and/or processing systems 100, 102 may be performed by a separate server system (not shown). Furthermore, one or more other services and/or systems not necessarily illustrated may be utilized in connection with implementing various aspects of the embodiments of the disclosed systems and methods. Although certain embodiments are discussed in connection with storing and transmitting genomic data, it will be appreciated that the disclosed embodiments may be further used in connection with efficiently storing any suitable type of information. Thus it will be appreciated that FIG. 1 is provided for purposes of illustration and explanation, and not limitation.

Figure 2:
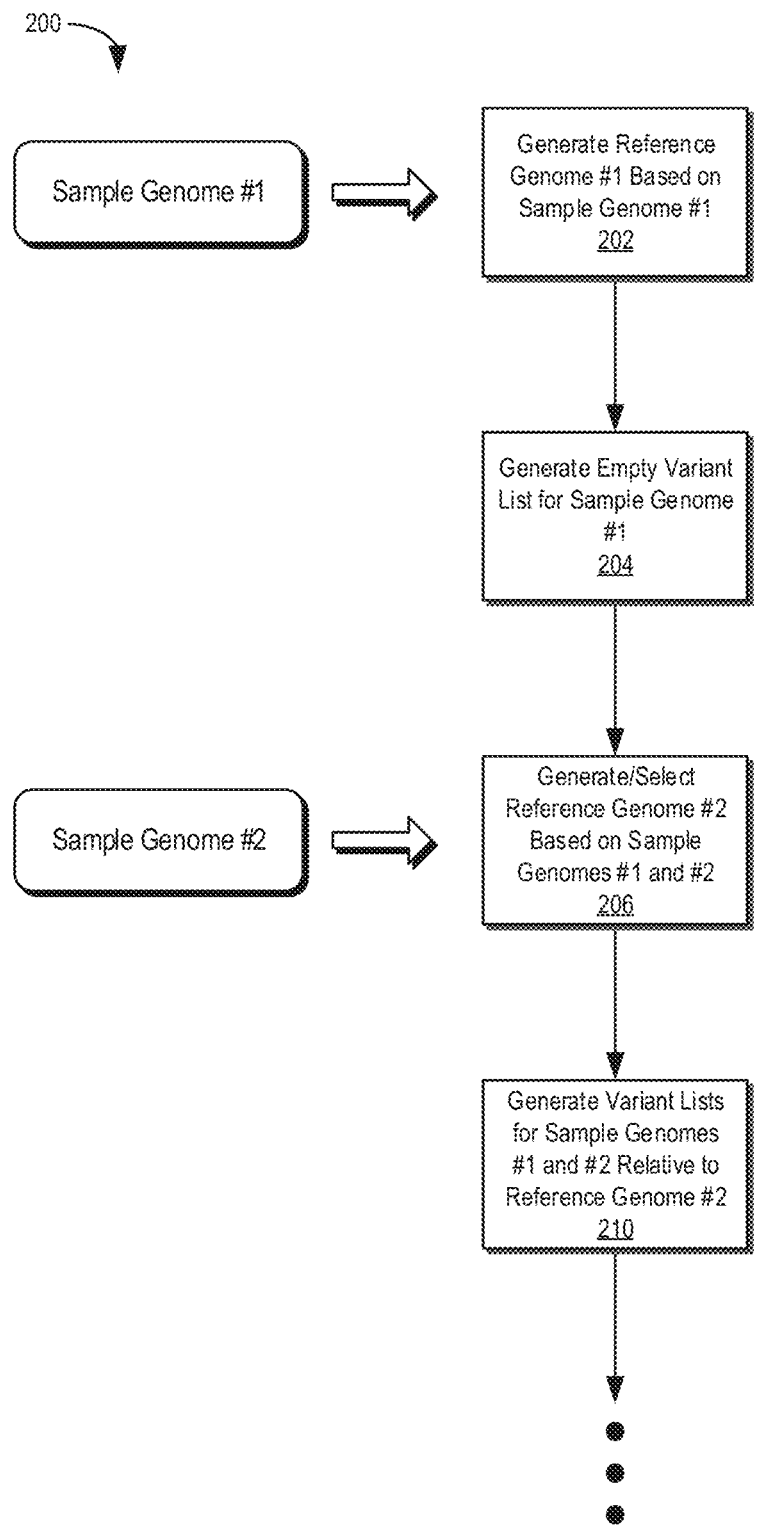
FIG. 2 illustrates a flow chart of an exemplary method for generating reference genome datasets and associated variant lists consistent with embodiments of the present disclosure.

FIG. 2 illustrates a flow chart an exemplary method 200 for generating reference genome datasets and associated variant lists consistent with embodiments of the present disclosure. The illustrated method 200 may be implemented in a variety of ways, including using software, firmware, hardware, and/or any combination thereof. In certain embodiments, various aspects of the method and/or its constituent steps may be performed by a genomic data storage and/or processing system and/or any other suitable system or combination of systems. In some embodiments, the illustrated method may facilitate the generation of one or more reference datasets and associated variant data that may be used to efficiently represent associated sample genomic data.

At 202, a first sample genome for transfer and/or storage may be designated as an initial reference genome. An empty variant list may be generated at 204 and associated with the first sample genome with a pointer to the initial reference genome (i.e., the first sample genome). The empty variant list may represent that the initial reference genome and the first sample genome are the same. That is, the empty variant list may indicate that there are no differences between the initial reference genome and the first sample genome.

Alternatively, a standard reference genome may be used as an initial reference genome (e.g., the CRCh38 genome and/or the like). A variant list may be generated associated with the first sample genome that includes a pointer to the standard reference genome. Entries in the variant list associated with the first sample genome may represent differences between the first sample genome and the standard reference genome. Accordingly, the first sample genome may be reconstructed using the standard reference genome and the entries in the variant list.

As new sample genomes are introduced in the database, the reference genome may be updated and/or otherwise regenerated at 206 such that the difference between the existing sample genomes in the database and the updated reference genome is of a minimum and/or otherwise reduced size. For example, as illustrated, an updated reference genome may be generated based on the first sample genome and a newly introduced second sample genome. In some embodiments, the updated reference genome may be generated in a manner such that the size of variant lists associated with the first sample genome and the second sample genome relative to the updated reference genome (e.g., the collective storage size of the lists) is minimized.

In some embodiments, generating an updated reference genome may include selecting an associated sample genome from the set of sample genomes included in the database to use as a new reference. For example, a standard reference genome may be used as an initial reference genome. After adding the sample genome and the second sample genome to the database, it may be determined that the second sample genome has fewer variants when compared against the first sample genome than when compared against the standard reference genome. Accordingly, the first sample genome may be selected as the updated reference genome, and a variant list associated with the second sample genome relative to the first sample genome (i.e., the updated sample genome) may be generated.

In further embodiments, an updated reference genome may be generated and/or otherwise selected based, at least in part, on contextual data associated with the sample genomes and/or available genomes that may be used as a reference genome (e.g., other sample genomes). Such contextual data may include, for example, comprise an indication of a relative genealogical and/or hereditary relatedness between individuals associated with various sample genomes and/or available reference genomes.

For example, a genome associated with a biological parent of a child may, given the relatively close genealogical and/or hereditary relatedness between a parent and child, be relatively similar to the genome of the child. Accordingly, the genome associated with the child may have fewer variants relative to the genome of the parent than a randomly selected reference genome. Accordingly, the genome of the parent may be selected as a reference genome for generating an associated variant list associated with the child consistent with various disclosed embodiments. Other contextual data associated with the sample genomes and/or available reference genomes relating to a relative genealogical and/or hereditary relatedness between individuals associated with the genomes may be similarly used in connection with selecting updated reference genomes consistent with embodiments disclosed herein.

Similarly, contextual data used in connection with generating and/or selecting an updated reference genome may comprise indications of an ethnic relatedness between individuals associated various sample genomes and/or available reference genomes. For example, a genome associated with a first individual of Nordic descent may have fewer variants relative to a genome associated with a second individual of Nordic descent than relative to a genome associated with a third individual of Mediterranean descent. Accordingly, the genome associated with the second individual may be selected as reference genome for generating a variant list associated with the genome of the first individual consistent with the disclosed embodiments.

Once the updated reference genome is generated and/or otherwise selected, variant lists associated with the first sample genome and/or second sample genome relative to the updated reference genome may be generated at 210. These variant lists may thus be used to reconstruct the first and second sample genomes based on the updated reference genome. Collectively, the variant lists and the updated reference genome may require less storage space and/or transmission bandwidth than the first sample genome and the second sample genomes in their entries. In this manner, the updated reference genome and variant lists may be stored and/or transmitted to a receiving system using less storage space and/or bandwidth than would be used if the original sample genomes were stored and/or transmitted.

Figure 3:
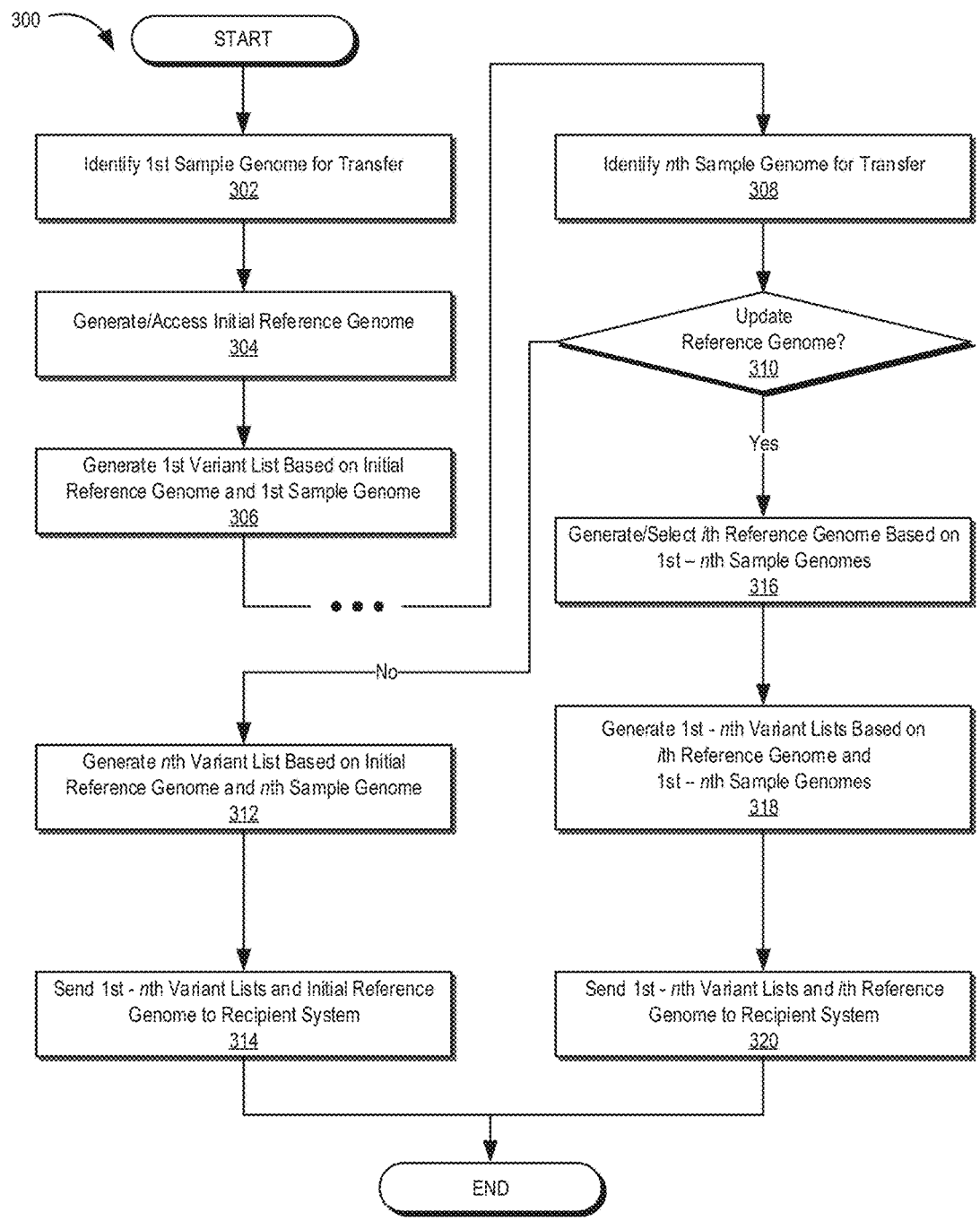
FIG. 3 illustrates a flow chart of an exemplary method of communicating genomic data consistent with embodiments of the present disclosure.

FIG. 3 illustrates a flow chart of an exemplary method 300 of communicating genomic data consistent with embodiments of the present disclosure. The illustrated method 300 may be implemented in a variety of ways, including using software, firmware, hardware, and/or any combination thereof. In certain embodiments, various aspects of the method and/or its constituent steps may be performed by a genomic data storage and/or processing system and/or any other suitable system or combination of systems.

At 302, a first sample genome may be identified for transfer to a receiving system. An initial reference genome may be accessed and/or generated at 304. As discussed above, in some embodiments, the first sample genome may be used as an initial reference genome. In further embodiments, a standard reference genome may be used as an initial reference genome (e.g., the CRCh38 genome and/or the like).

A first variant list associated with the first sample genome may be generated at 306 based on the initial reference genome and the first sample genome. In some embodiments, the first variant list may include information indicative of differences between the first sample genome and the initial reference genome. In this manner, the first variant list may be used in connection with the initial reference genome to reconstruct the first sample genome. For example, in some embodiments, a variant list may include a position where a variant occurs and an indication of what the associated variant is (e.g., a specific allele occurring at an indicated variant position).

At 308, an $n^{th}$ sample genome may be identified for transfer to a receiving system. A determination may be made at 310 whether the initial reference genome should be updated in connection with generating an $n^{th}$ variant list representative of the $n^{th}$ sample genome. In some embodiments, an updated reference genome may be generated whenever new sample genomes are identified for storage and/or transmission. In further embodiments, an updated reference genome may not necessarily be generated at every instance a new sample genome is identified for storage and/or transmission. For example, as the number of sample genomes represented in a genomic dataset to be stored and/or transferred increases, the computation required to compute an updated reference genome may become progressively more computationally complex. Updated reference genomes may thus be generated periodically, following the introduction of a certain number of new sample genomes for storage and/or transmission, and/or at any other suitable time.

In certain embodiments, heuristic methods may be used to determine when a net reduction in storage size and/or bandwidth used to communicate the set of sample genomes in the database and/or subsets thereof would benefit from computation of an updated reference genome. In some embodiments, such methods may compare an estimate of an amount of time and/or processing resources required to generate and/or select an updated reference genome with an estimated net reduction in storage size and/or bandwidth to determine whether a reference genome should be updated.

If it is determined at 310 that the initial reference genome does not need to be updated, the method 300 may proceed to 312, where an $n^{th}$ variant list may be generated based on the initial reference genome and the $n^{th}$ sample genome. The $n^{th}$ variant list may include information indicative of differences between the $n^{th}$ sample genome and the initial reference genome, and may be used in connection with the initial reference genome to reconstruct the $n^{th}$ sample genome.

At 314, the first-$n^{th}$ variant lists may be communicated to an intended recipient system. In some embodiments, the initial reference genome may further be communicated to the recipient system. In certain embodiments, rather than sending the entire initial reference genome, a link and/or other reference to the initial reference genome that may be used by the recipient system to access the initial reference genome may be sent. Transmitting a link and/or location of a reference genome may speed the transmission of associated genomic data (e.g., sample genomic data sets), allowing the reference genome to be accessed on an as-needed basis. In some embodiments, this increased transmission speed may be beneficial when a set of genomic data samples is represented by multiple reference genomes, as discussed in more detail below.

If it is determined at 310 that the initial reference genome needs to be updated, the method may proceed to 316. At 316, an updated reference genome (i.e., an ith reference genome) may be generated. In some embodiments, the ith reference genome may be generated based on the $1^{st}$-$n^{th}$ sample genomes. In certain embodiments, the $i^{th}$ reference genome may be generated in a manner such that the size of the variant lists associated with the $1^{st}$-$n^{th}$ sample genomes relative to the $i^{th}$ reference genome (e.g., the collective storage size of the lists) is reduced and/or otherwise minimized.

In some embodiments, a plurality of reference genomes may be maintained, with each variant list associated with individual sample genomes referencing and/or otherwise pointing to a related reference genome of the plurality of reference genomes. As an example, a first set of sample genomes may reference a first reference genome and a second set of sample genomes may reference a second reference genome. The first set of sample genomes may be reconstructed using associated variant lists and the first reference genome, and the second set of sample genomes may be reconstructed using associated variant lists and the second reference genome. In this manner, rather than recalculating a reference genome across an entire set of sample genomes, reference genomes may be generated and associated with a subset of sample genomes, thereby providing certain computational and/or processing efficiencies.

In certain embodiments, an individual sample genome may be associated with a plurality of references and/or variant lists. For example, a first portion of a sample genome may be relatively similar to a first reference. Accordingly, the first reference may be used to generate a first variant list associated the first portion of the sample genome. A second portion of the sample genome may be more similar to a second reference than it is to the first reference. Accordingly, the second reference may be used to generate a second variant list associated with the second portion of the sample genome. In this manner, various portions of the individual sample genome may be represented by different variant lists and/or different reference genomes.

In various embodiments where multiple reference genomes are used, a set of reference genomes may be stored as a base reference genome and a set of differences (i.e., variants) relative to the base reference genome. Any given reference genome may, therefore, be reconstructed by applying its associated variants to the base reference genome. Among other things, representing a set of reference genomes as a set of variants from a base reference genome may allow for efficiencies in the storage and/or communication of the reference genomes.

At 318, first-$n^{th}$ variant lists associated with the first-$n^{th}$ sample genomes may be generated based on the first-$n^{th}$ sample genomes and the $i^{th}$ reference genome. The $1^{st}$-$n^{th}$ variant lists may include information indicative of differences between the first-$n^{th}$ sample genomes and the $i^{th}$ reference genome. In this manner, the first-$n^{th}$ variant lists may be used in connection with the $i^{th}$ reference genome to reconstruct the first-$n^{th}$ sample genomes.

At 320, the first-$n^{th}$ variant lists may be communicated to an intended recipient system. In some embodiments, the $i^{th}$ reference genome may further be communicated to the recipient system. In certain embodiments, rather than sending the entire $i^{th}$ reference genome, a link and/or other reference to the $i^{th}$ reference genome may be sent that may be used by the recipient system to access the initial reference genome. In embodiments utilizing a plurality of reference genomes, the $i^{th}$ reference genome may be communicated as a list of variants relative to an $i^{th}$ reference genome and/or another reference genome (e.g., an $i^{th}$-1 reference genome or the like). Based on the communicated variant list, the $i^{th}$ reference genome may be reconstructed by a recipient system.

Certain embodiments disclosed herein may operate as a version control system. A baseline state may be represented with a revision number, and each subsequent state may be represented by the variants and/or "diffs" between the base state and the subsequent state. To reconstruct an $n^{th}$ revision, the set of variants for each revision may be applied to the baseline until a desired revision is reached. For example, an initial reference genome may be used as a baseline state. Each subsequent update of the reference genome may be represented as a list of variants between the previous version and the current revision. Any revision of the reference genome may thus be computed from another revision of the reference genome and the set of variants and/or "diffs" for all revisions in between.

In conjunction with the storage and/or management of variant lists associated with sample genomes, associated quality scores may also be maintained. Quality scores may represent a relative confidence in a particular read of a sequence location in a genome performed by a genetic sequencing system. This may be based, at least in part, on a location of the sequence location on a sequenced strand of DNA (e.g., the ends, the middle, etc.). In certain embodiments, quality scores associated with a particular sample genome may be used in conjunction with an associated variant list and reference to reconstruct a genomic dataset sequencing associated with the sample.

It will be appreciated that a number of variations can be made to the method presented in connection with FIG. 3 within the scope of the inventive body of work. For example, as discussed above, in certain embodiments, a plurality of reference genomes may be used, each reference genome of the plurality of reference genomes being used in connection with representing a subset of a set of sample genomes based on associated variant lists. Thus it will be appreciated that FIG. 3 is provided for purposes of illustration and explanation, and not limitation.

Figure 4:
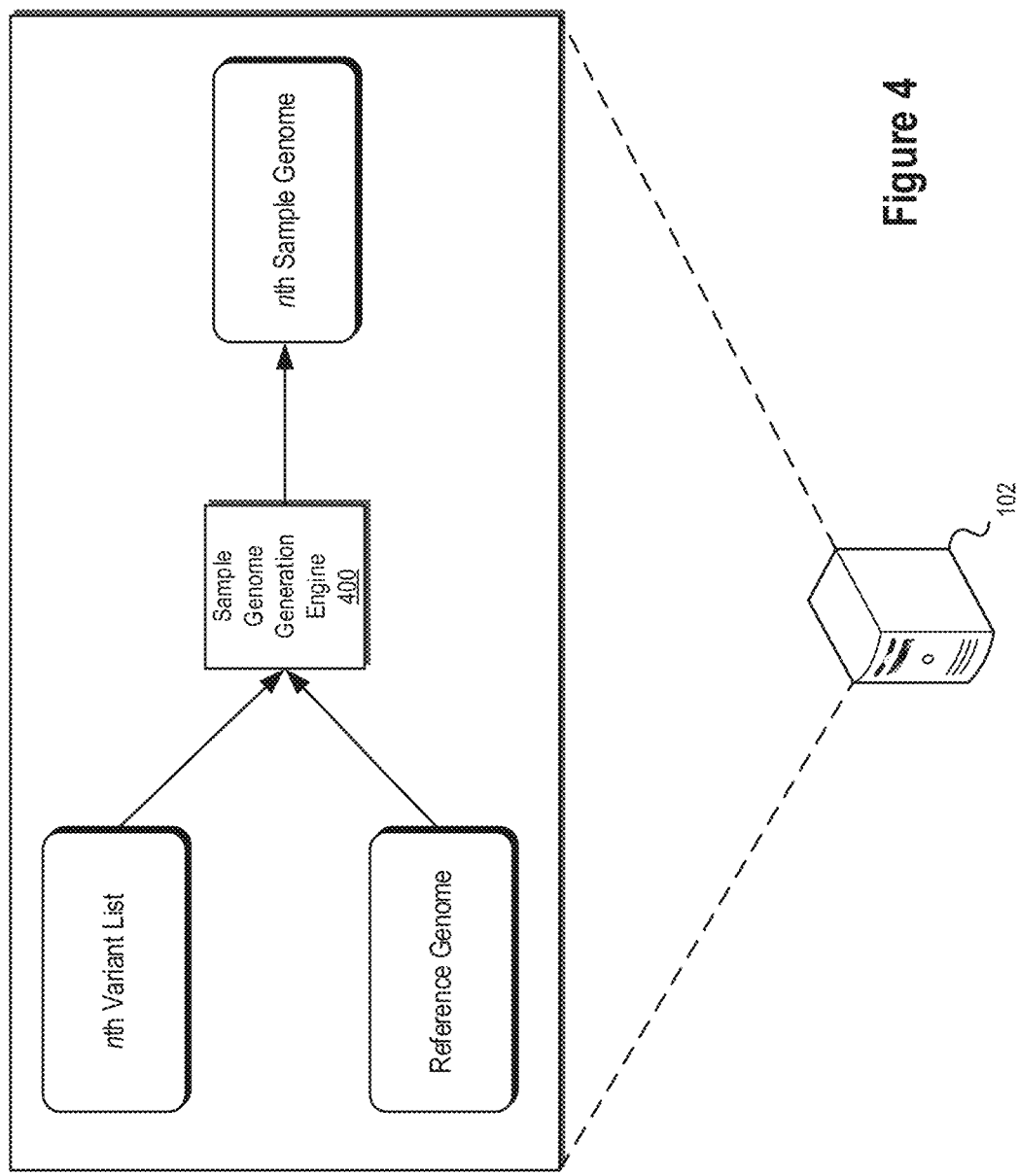
FIG. 4 illustrates generation of a sample genomic dataset based on an associated variant list and a reference dataset consistent with embodiments of the present disclosure.

FIG. 4 illustrates generation of a sample genomic dataset based on an associated variant list and a reference genome consistent with embodiments of the present disclosure. Aspects of the illustrated process may be implemented in a variety of ways, including using software, firmware, hardware, and/or any combination thereof. In certain embodiments, a genomic data storage and/or processing system 102 may receive and store a variant list representative of a sample genomic dataset and/or a reference genome. For example, as illustrated, the genomic data storage and/or processing system 102 may receive and/or store an nth variant list representative of an $n^{th}$ sample genomic dataset.

A sample genome generation engine 400 executing on the genomic data storage and/or processing system 102 may receive and/or otherwise access the $n^{th}$ variant list and an associated reference genome. In some embodiments, the reference genome may be identified by a pointer reference included in the $n^{th}$ variant list. Based on the $n^{th}$ variant list and the identified reference genome, the sample genome generation engine 400 may regenerate the $n^{th}$ sample genome represented by the $n^{th}$ variant list. For example, sample genome generation engine 400 may apply "cliffs" represented in the $n^{th}$ variant list to the reference genome to generate the $n^{th}$ sample genome.

Figure 5:
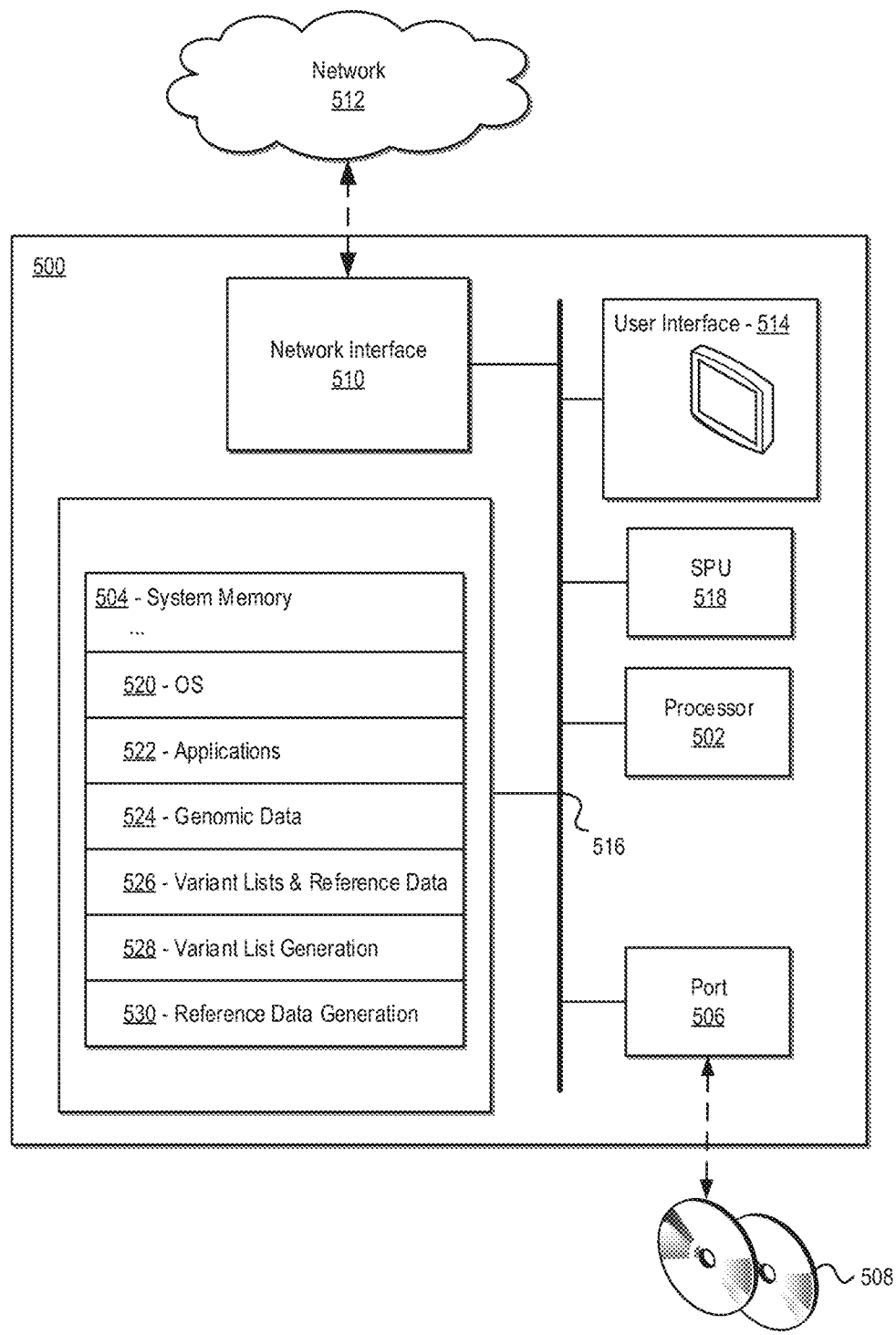
FIG. 5 illustrates an exemplary system that may be used to implement embodiments of the systems and methods of the present disclosure.

FIG. 5 illustrates an exemplary system 500 that may be used to implement embodiments of the systems and methods of the present disclosure. Certain elements associated with the illustrated exemplary system 500 may be included in one or more systems configured to store, communicate, and/or otherwise use genomic data, and/or any other system configured to implement embodiments of the disclosed systems and methods. As illustrated in FIG. 5, the system 500 may include: a processing unit 502; system memory 504, which may include high speed random access memory ("RAM"), non-volatile memory ("ROM"), and/or one or more bulk non-volatile non-transitory computer-readable storage mediums (e.g., a hard disk, flash memory, etc.) for storing programs and other data for use and execution by the processing unit 502; a port 506 for interfacing with removable memory 508 that may include one or more diskettes, optical storage mediums, and/or other non-transitory computer-readable storage mediums (e.g., flash memory, thumb drives, USB dongles, compact discs, DVDs, etc.); a network interface 510 for communicating with other systems via one or more network connections 512 using one or more communication technologies; a user interface 514 that may include a display and/or one or more input/output devices such as, for example, a touchscreen, a keyboard, a mouse, a track pad, and the like; and one or more busses 516 for communicatively coupling the elements of the system.

In some embodiments, the system may, alternatively or in addition, include an SPU 518 that is protected from tampering by a user of the system or other entities by utilizing secure physical and/or virtual security techniques. An SPU 518 can help enhance the security of sensitive operations such as personal information management, trusted credential and/or key management, privacy and policy management, versioning control and/or management, and other aspects of the systems and methods disclosed herein. In certain embodiments, the SPU 518 may operate in a logically secure processing domain and be configured to protect and operate on secret information, as described herein. In some embodiments, the SPU 518 may include internal memory storing executable instructions or programs configured to enable the SPU 518 to perform secure operations, as described herein.

The operation of the system 500 may be generally controlled by the processing unit 502 and/or the SPU 518 operating by executing software instructions and programs stored in the system memory 504 (and/or other computer-readable media, such as removable memory 508). The system memory 504 may store a variety of executable programs or modules for controlling the operation of the system. For example, the system memory may include an operating system ("OS") 520 that may manage and coordinate, at least in part, system hardware resources and provide for common services for execution of various applications and a trust and privacy management system for implementing trust and privacy management functionality including protection and/or management of personal data through management and/or enforcement of associated policies. The system memory may further include, without limitation, communication software configured to enable in part communication with and by the system; one or more applications 522; genomic data 524; variant lists and/or reference data 526 associated with the genomic data; one or more modules for generating sample variant lists 528, reference genomes, and/or reference genome variant lists 530; and/or any other information, modules, and/or applications configured to implement embodiments of the systems and methods disclosed herein.

The systems and methods disclosed herein are not inherently related to any particular computer, device, service, or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers, at one site or distributed across multiple sites and interconnected by a communication network.

Software embodiments may be implemented as a computer program product that comprises a non-transitory storage medium configured to store computer programs and instructions, that when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, an optical storage medium, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing both the systems and methods described herein. Accordingly, the present embodiments are to be considered as illustrative and not restrictive, and the invention is not to be limited to the details given herein, but may be modified within the scope and equivalents of the appended claims.

What is claimed is:

1. A method for communicating genomic information performed by a first computing system comprising a processor and a non-transitory computer-readable medium storing instructions that, when executed by the processor, cause the processor to perform the method, the method comprising:
   receiving a first sample genomic dataset for transfer to a second computing system;
   generating a first reference dataset;
   generating, based on the first sample genomic dataset and the first reference dataset, a first variant list, the first variant list comprising entries indicating differences between the first sample genomic dataset and the first reference dataset;
   receiving an nth sample genomic dataset for transfer to the second computing system;
   generating, based on the first sample genomic dataset and the nth sample genomic dataset, an ith reference dataset;
   generating, based on at least the first sample genomic dataset and the ith reference dataset, an updated first variant list comprising entries indicating differences between the first sample genomic dataset and the ith reference dataset;
   generating, based on the nth sample genomic dataset and the ith reference dataset, an nth variant list comprising entries indicating differences between the nth sample genomic dataset and the ith reference dataset; and
   transmitting the first variant list and the nth variant list from the first computing system to the second computing system.

2. The method of claim 1, wherein generating the first reference dataset comprises assigning the first sample genomic dataset as the first reference dataset.

3. The method of claim 2, wherein entries of the first variant list comprise null values.

4. The method of claim 1, wherein generating the first reference dataset comprises accessing a standard genomic reference dataset.

5. The method of claim 1, wherein the first variant list comprises a reference to the first reference dataset.

6. The method of claim 1, wherein the nth variant list comprises a reference to the ith reference dataset.

7. The method of claim 1, wherein prior to generating the ith reference dataset, the method further comprises determining that an updated reference dataset should be generated.

8. The method of claim 7, wherein determining that the updated reference dataset should be generated comprises determining that a threshold number of sample genomic datasets are represented using the first reference dataset.

9. The method of claim 7, wherein determining that the updated reference dataset should be generated comprises determining that a size of a variant list generated based on the first reference dataset and the nth sample genomic dataset exceeds a threshold size.

10. The method of claim 7, wherein determining that the updated reference dataset should be generated comprises determining that a collective size of variant lists generated based on the first reference dataset and the nth sample genomic dataset exceeds a threshold size.

11. The method of claim 1, wherein the method further comprises transmitting the ith reference dataset from the first computing system to the second computing system.

12. The method of claim 1, wherein the method further comprises generating an ith reference variant list comprising entries indicating differences between the ith reference dataset and the first reference dataset.

13. The method of claim 12, wherein the method further comprises transmitting the ith reference variant list from the first computing system to the second computing system.

14. The method of claim 1, wherein generating the ith reference dataset is further based on contextual information associated with the first sample genomic dataset and the nth sample genomic dataset.

15. The method of claim 14, wherein the contextual information comprises an indication of a genealogical relatedness between an individual associated with the first sample genomic dataset and an individual associated with the nth sample genomic dataset.

16. The method of claim 14, wherein the contextual information comprises an indication of an ethnical relatedness between an individual associated with the first sample genomic dataset and an individual associated with the nth sample genomic dataset.

17. The method of claim 1, wherein generating the ith reference dataset comprises selecting the ith reference dataset from one or more existing genomic datasets.

* * * * *